US008942811B2

(12) United States Patent
Gardin et al.

(10) Patent No.: US 8,942,811 B2
(45) Date of Patent: Jan. 27, 2015

(54) TRANSCRANIAL CURRENT STIMULATION DEVICE AND METHOD

(75) Inventors: Paul Gardin, Ottawa (CA); Mathieu Lemay, Ottawa (CA); Daniel Shapiro, Ottawa (CA); Ian Chapman, Gatineau (CA); Shazib Shaukat, Ottawa (CA); Stanley Shapiro, Sudbury (CA); Brian Dressler, Sudbury (CA)

(73) Assignee: Nuraleve Inc., Ottawa, Ontario (CA)

( * ) Notice: Subject to any disclaimer, the term of this patent is extended or adjusted under 35 U.S.C. 154(b) by 0 days.

(21) Appl. No.: 13/548,241

(22) Filed: Jul. 13, 2012

(65) Prior Publication Data
US 2014/0018881 A1 Jan. 16, 2014

(51) Int. Cl.
A61N 1/37 (2006.01)
A61N 1/36 (2006.01)
A61N 1/08 (2006.01)

(52) U.S. Cl.
CPC ... *A61N 1/36* (2013.01); *A61N 1/08* (2013.01); *A61N 1/36025* (2013.01)
USPC .............................................. 607/45; 607/46

(58) Field of Classification Search
CPC ... A61N 1/36; A61N 1/3605; A61N 1/36021; A61N 1/0534; A61N 1/36025; A61N 1/0531; A61N 1/0529; A61N 1/3718; A61N 1/08
USPC .................................................... 607/45, 46
See application file for complete search history.

(56) References Cited

U.S. PATENT DOCUMENTS 3,534,353 A 10/1970 Calkin et al.
5,433,732 A * 7/1995 Hirschberg et al. ............... 607/7
6,067,217 A 5/2000 Kida et al.
8,170,682 B2 5/2012 Greenberg et al.
8,565,869 B2 * 10/2013 Lee et al. ........................ 607/2
2011/0288610 A1 * 11/2011 Brocke ........................ 607/45

OTHER PUBLICATIONS

M. Bikson, A. Datta, M. Elwassif, "Establishing safety limits for transcranial direct current stimulation", Clinical Neurophysiology, vol. 120(6), Jun. 2009.
Brochure listing capabilities of a typical competing tDCS device: neuroConn DC-Stimulator Brochure.
Example of a passive alternative to limit current: Datasheet for Littelfuse Radial Lead Micro Fuse 272/273/274/278/279 Series.
Linear Technology, "Current Sense Circuit Collection", Application Note AN105, Dec. 2005.
Microchip Inc., "Current Sensing Circuit Concepts and Fundamentals", Application Note AN1332, 2011.
M.A. Nitsche and W. Paulus, "Transcranial direct current stimulation—update 2011", Restorative neurology and neuroscience, vol. 29, No. 6, pp. 463-492, Nov. 2011.
M.A. Nitsche, D. Liebetanz, N. Land, A. Antal, F. Tergau, W. Paulus, "Safety criteria for transcranial direct current stimulation (tDCS) in humans", Clinical Neurophysiology vol. 114 pp. 2220-2222, 2003.

* cited by examiner

Primary Examiner — Tammie K Heller

(57) ABSTRACT

A device for transcranial stimulation. The device for transcranial stimulation comprises an adjustable current source for providing a stimulation current; a first electrode connected to the current source for electrical connection to a patient; a second electrode connected to the current source for electrical connection to the patient; a first current interruptor for interrupting current flow between the current source and the electrode, the first current interruptor connected between the adjustable current source and the first electrode; and an output monitor connected between the current source and the first electrode for monitoring current to the patient. The output monitor detects an abnormal current it signals the first interruptor, which interrupts the current to the patient. A method of operating a device for transcranial stimulation is also provided.

5 Claims, 3 Drawing Sheets

# TRANSCRANIAL CURRENT STIMULATION DEVICE AND METHOD

BACKGROUND OF THE INVENTION

1. Field of the Invention

The invention relates to electrical stimulation of the body, and in particular a system, device and method for controlled and monitored electrical transcranial stimulation using cutaneous electrodes for medical treatment applications.

2. Description of the Prior Art

Transcranial Direct Current Stimulation (tDCS) is a method of applying low current electrical signals across the head in order to affect cognitive processes in a patient's brain as part of a medical treatment. Specifically, tDCS treatment is typically applied with currents in the 0 to 10 milliamperes (0 to 0.010 amperes) range. tDCS treatment has numerous medical applications that include treatment of drug addiction, post-stroke rehabilitation and treatment of depression.

tDCS treatment sessions are generally applied using a device containing a current source, such that a predictable amount of treatment current can be delivered to the patient, regardless of the impedance of the electrical pathway between a set of cutaneous electrodes. The device may be capable of generating differential output voltages of up to 80 volts or more.

In order to ensure the safety of the patient, it is necessary to ensure that the output current of the tDCS device does not exceed a safe level. If, due to a failure of electronics or programming, the output current were to exceed the prescribed safe level, serious injury to the patient could result, including damage to the patient's skin and brain.

In the past, fuses have been used as a safety means on electrical lines to provide overcurrent protection. However, due to the low currents used in tDCS treatments, fuses alone are not able to provide adequate protection to the patient, as there are no fuses on the market able to quickly interrupt a current of such small magnitude. Similarly, given that the range of safe tDCS currents may be narrow, fuses do not provide an adequately accurate threshold for protection. Fuses also cannot provide a nuanced approach to detecting abnormal conditions.

To ensure absolute safety of the patient receiving tDCS, there is a need for a reliable method of preventing the output current of the tDCS device from exceeding a pre-determined safe level, even in the presence of component failures, programming faults or abnormal circumstances. A system and method for preventing tDCS treatment current from exceeding a given level, even in the presence of multiple component failures is presented herein.

SUMMARY OF THE PRESENT INVENTION

A device for transcranial stimulation is provided, comprising an adjustable current source for providing a stimulation current; a first electrode connected to the current source for electrical connection to a patient; a second electrode connected to the current source for electrical connection to the patient; a first current interruptor for interrupting current flow between the current source and the electrode, the first current interruptor connected between the adjustable current source and the first electrode; an output monitor connected between the current source and the first electrode for monitoring current to the patient, wherein when the output monitor detects an abnormal current it signals the first interruptor, which interrupts the current to the patient.

Further disclosed is the device further comprising a second current interruptor for interrupting current flow between the current source and the electrode connected between the adjustable current source and the second electrode. Further the device is provided further comprising a return monitor connected between the current source and the second interruptor for monitoring the current from the patient.

In one embodiment, the device further comprises an error detector, wherein the output monitor and return monitor are in communication with the error detector, and the error detector provides a signal to at least one of the first and second interrupters to interrupt the current when an abnormal current is detected by at least one of the monitors. The device is provided wherein the error detector comprises a comparator to compare the difference of the signals of the output monitor and return monitor.

In an embodiment, the device is provided wherein the error detector indicates normal operation with a high signal and abnormal operation with a low signal, such that if the error detector receives no power an abnormal operation is signaled. The device is provided wherein the error detector is a latching error detector for holding the device in an interrupted state if an error occurs during operation. Further, the device is provided wherein the latching cannot be reset while an error condition is ongoing. Also, the device is provided further comprising an error counter in communication with the controller, for monitoring frequency of errors.

A method of operating a device for transcranial stimulation is disclosed, comprising the steps of turning the device on to initialize the device; applying electrodes connected to the device to a patient; continuously applying and monitoring an output current; and interrupting the current to the patient if the output current is abnormal. An embodiment of the method further comprises the steps of continuously monitoring a return current; and interrupting the current to the patient if the return current is abnormal.

The method is provided further comprising the steps of interrupting the current to the patient if a comparison of the output current to the return current is abnormal. In an embodiment the method further comprises the step of interrupting the current to the patient when the microcontroller signals an interrupted state.

Also provided is the method further comprising the step of engaging a latch circuit for holding the device in an interrupted state until the device is reset. The method is provided wherein the current is interrupted by one or more interrupters. In an embodiment, the method is provided further comprising the steps of continuously monitoring the output voltage; interrupting the current to the patient if the output voltage is abnormal. Further disclosed is the method, further comprising the step of interrupting the current to the patient when the output voltage divided by the output current is abnormal. The method is provided wherein the current is interrupted by one or more fuses.

DETAILED DESCRIPTION OF THE PRESENT INVENTION

The present invention will now be described more fully hereinafter with reference to the accompanying drawings, in which preferred embodiments of the present invention are shown. This invention may however, be embodied in many different forms and should not be construed as limited to the embodiments set forth herein. Rather, these embodiments are provided so that this application will be thorough in illustrations and brief explanation therefore to convey the true scope of the invention to those skilled in the art. Some illustrations provided herein include detailed explanations of dimension and operation and as such should not be limited thereto.

Overview

The present invention, a safety mechanism for a Transcranial Direct Current Stimulation (tDCS) medical device, is a system and method for ensuring that electrical output current from a tDCS device cannot exceed a pre-determined safe level in the event of a component failure, programming error or other unintended fault condition. This safety system is intended as part of a complete tDCS device using circuitry fabricated with industry standard printed circuit board (PCB) manufacturing methods.

The present invention incorporates multiple, independent circuits for detecting abnormal conditions of the tDCS electrical output. These circuits provide capability to measure electrical current and electrical voltage, circuits to detect when these measurements are outside normal parameters and circuits to lock the tDCS device into a disabled condition if abnormal conditions are detected. When locked into a disabled condition, the patient undergoing tDCS treatment will be electrically isolated in reference to the circuitry inside the tDCS device and will experience no current from the tDCS device.

Function

Figure 1:
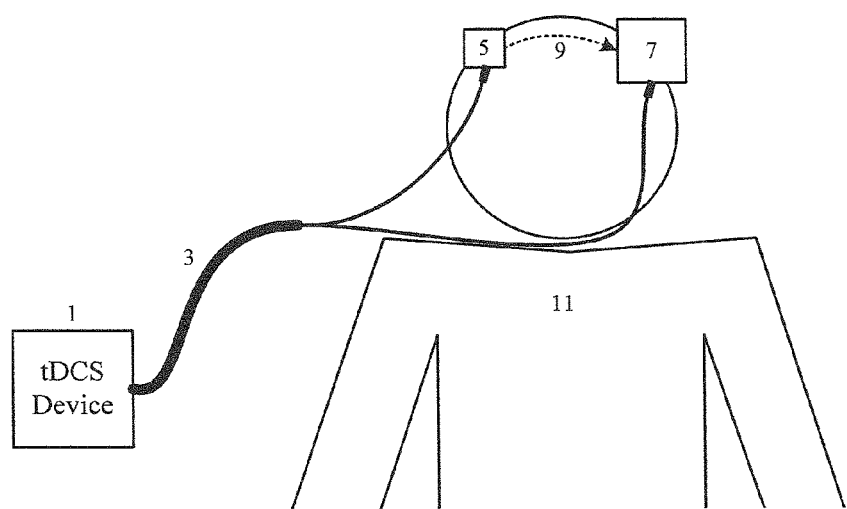
FIG. 1 shows a schematic illustration of the tDCS treatment of the present invention.

One configuration for tDCS treatment is illustrated in FIG. 1. A tDCS device 1, containing a current source, passes a mild electrical current (typically between 0 and 10 mA) through a lead cable 3 to the head of a human patient 11. The current passes through an anode electrode 5, takes various paths 9 through the patient, and returns to a cathode electrode 7. From the cathode electrode 7, the current returns to the tDCS device 1 through the lead cable 3. Through this mechanism, the cortical excitability in the brain of the patient 11 may be affected for various medical treatment purposes.

Figure 2:
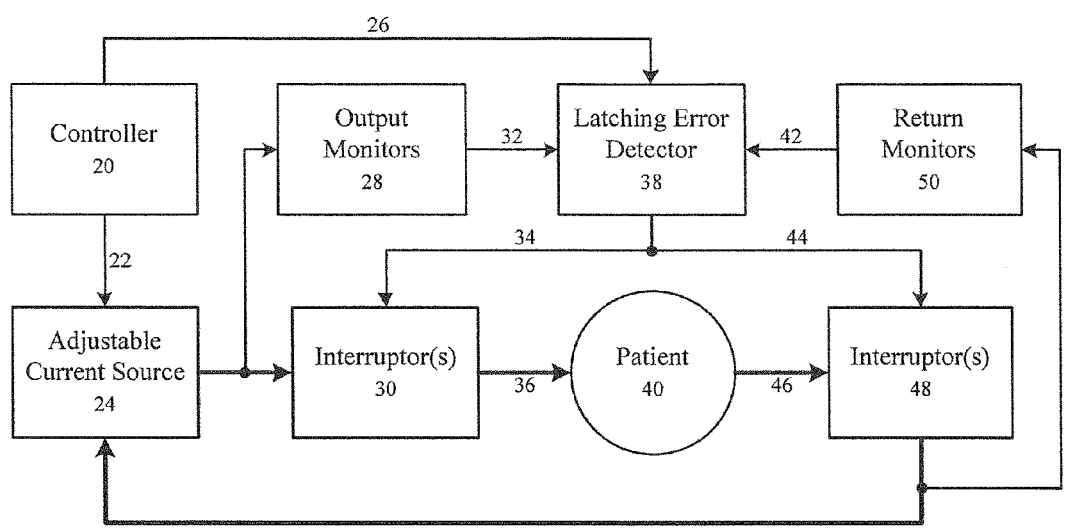
FIG. 2 shows a flowchart of the tDCS treatment of the present invention.

With reference to FIG. 2, an overview is shown of a system for ensuring the tDCS treatment current is within safe voltage and current parameters and for isolating the patient from the device if these pre-determined parameters are violated. An adjustable current source 24 is used to create the correct amount of tDCS output voltage to hold the programmed amount of output current depending on the amount of impedance along the current path leading through the patient. The amount of output current being used may be set by a controller 20 using control signals 22. The controller 20 may be a microcontroller unit (MCU), field-programmable gate array (FPGA), another computing device, a set of controls operated by a human or a combination thereof.

The output current from the current source 24 passes through a first interruptor 30, a mechanism for interrupting the current path, through the patient 40, and through a second interruptor 48, before returning to the device. Interruptors 30 and 48 may be mechanical relays, solid state switches or other electronically controlled switching technology. Solid state devices for 30 and 48 are preferred for their higher reliability, lower power consumption and faster operating speed in comparison to mechanical relays. Interruptors 30 and 48 are wired such that they have closed and open states, wherein the closed state results in an electrical connection through the interruptors 30, 48, and in an open state, the connections to the patient 36 and 46 are electrically floating and isolated in reference to the rest of the device, preventing transmission of a current from the device through the patient.

Control of the interruptors 30 and 48 is governed by a latching error detector 38, via control signals 34 and 44. The function of the latching error detector 38 is to monitor a set of input signals such as along 26, 32 and 42 in order to determine if they are within a pre-determined normal range. The signals may include, but are not limited to, current and voltage measurements. If said signals are not within this normal range, the latching error detector 38 will isolate the patient 40 from the rest of the device by de-activating mechanisms 30 and 48 via control signals 34 and 44, so as to put interruptors 30, 40 in an open state. The latching error detector 38 will leave the device in this de-activated state until it is reset—even if the original triggering condition has disappeared. The reset may occur automatically after the expiration of a predetermined amount of time, or occur as a result of cycling the tDCS device 1 off and on. The controller 120 may reset the latch under a number of conditions, such as pressing of a reset button (not shown), the expiry of a time period, or the disconnection of the electrodes from the person. Alternatively, an embodiment may have no latching error detector 38 at all, wherein the output will reconnect automatically once the error disappears, however has the drawback of potential oscillation of the system between connecting and disconnecting as a result of an error, which may be dangerous to the patient 40 and harmful to the tDCS device 1.

Critical parameters of the output current are sensed both before the current exits the device and after the current returns to the device, using pre- and post-monitors 28 and 50 respectively. For example, in one embodiment, maximum output current may be specified as up to 4 milliamperes nominal, with a limit set a small percentage above this, such as 4.1 milliamperes. Similarly, in an embodiment where power supply 110 outputs 30 volts nominal, a limit on the voltage at path 135 may be set above the specified upper tolerance of power supply 110, such as at 33 volts. In one embodiment both monitors 28 and 50 contain circuits to read the voltage and the current being applied to the patient 40 and to output a representation of those parameters in a way that is understandable to latching error detector 38 via signals 32 and 42. The controller 120 may also read parameters including current and voltage being applied to the patient 40, via analog to digital converter modules (not shown). This capability allows the controller 120 to keep a record of the treatment and to make any additional logical determinations about the safety and efficacy of the output in parallel to the monitoring provided by the circuits in FIG. 3.

Interruption of the current may be accomplished by breaking the path between the current source and the patient, breaking the path returning from the patient to the device, greatly increasing the resistance in the current path, closing an alternative low resistance current path within the device to shunt excess current, disabling the power supply that powers the current source, disabling the current source, shutting down power to the whole device, or a combination thereof.

Figure 3:
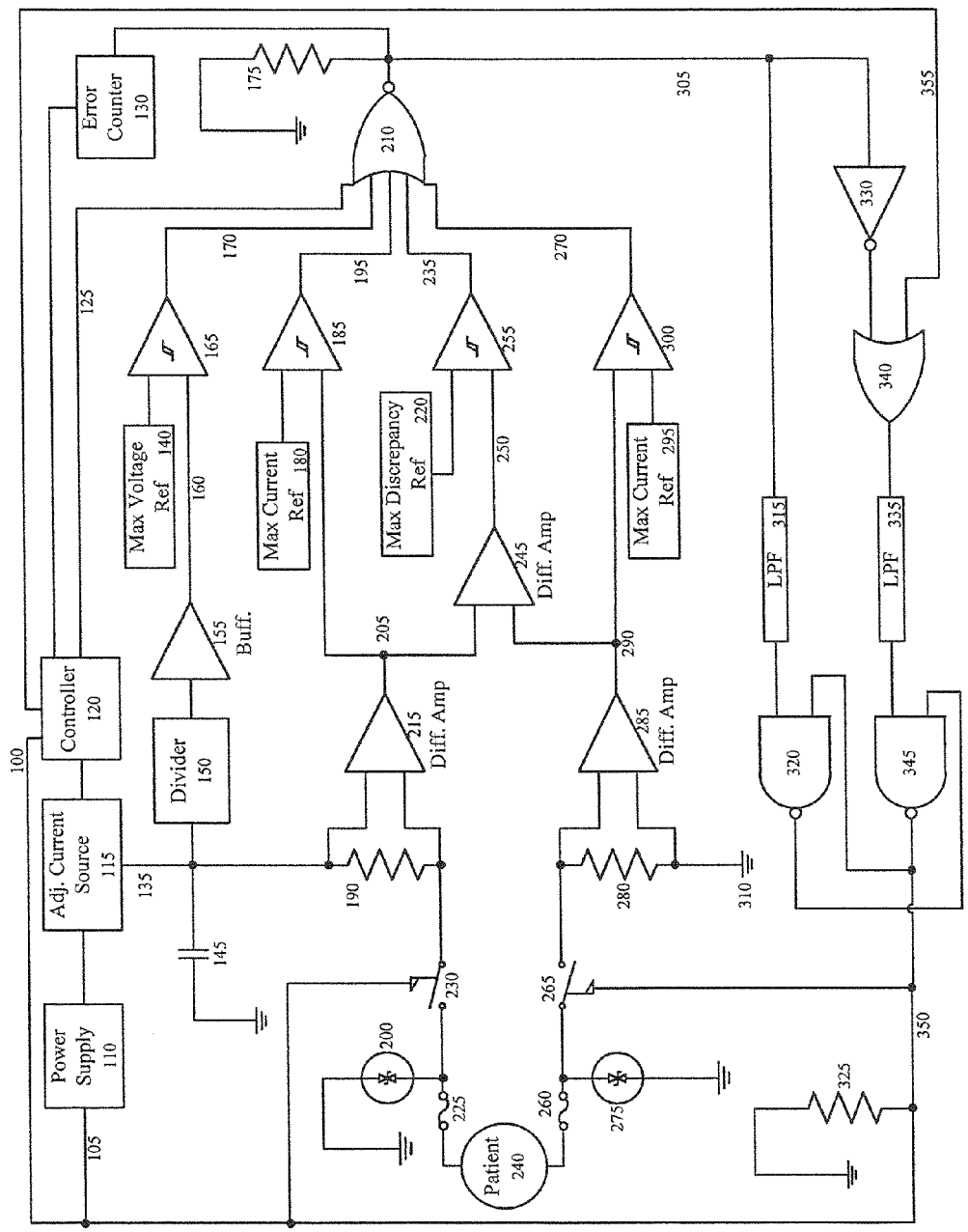
FIG. 3 depicts a schematic diagram for an embodiment of the functionality presented in FIG. 2 of the present invention.

FIG. 3 depicts a schematic diagram for an embodiment of the functionality presented in FIG. 2. In this embodiment, an adjustable current source 115 outputs a programmed amount of current via path 135 by regulating power from power supply 110, according to the amount of output current programmed by controller 120. A capacitor 145 at the output of current source 115 is used as a method to slow down any sudden changes in the output that may occur. The output monitoring components 140, 150, 155, 165, 180, 185, 190 and 215 in FIG. 3 represent a possible embodiment of the output monitor 28 in FIG. 2. The return monitoring components 280, 285, 295 and 300 in FIG. 3 represent a possible embodiment of the return monitor 50 in FIG. 2. Error detecting and latching components 175, 210, 245, 255, 315, 320, 325, 330, 335 and 340 in FIG. 3 represent a possible embodiment of the latching error detector 38 in FIG. 2. The voltage being output by the current source 115 is electronically measured using a chain consisting of a divider 150, a buffer 155 and a comparator 165. The voltage output from the current source 115 may occupy a wide range, potentially between 0 volts and 80 volts. A divider circuit 150 configured to have a very high input impedance is used to scale this wide output voltage down to a smaller range that is more easily compatible with low power electronic measurement. For example, a particular device embodiment may use an output voltage in the range of 0 volts to 30 volts, and may use measurement electronics that operate in a range of 0 volts to 3 volts. In this case, the divider 150 would be configured to scale the voltage down by a factor of ten or more. A buffer 155 is used to further increase the impedance between the output voltage and any following measurement circuitry to reduce the detrimental effect that measurement would have on the output and to increase the accuracy of the measurement.

Note that the order of the divider 150 and the buffer 155 can be switched, when using a buffer 155 that is capable of higher voltage operation. The configuration shown uses a lower voltage buffer 155 in order to reduce device battery/power consumption at the cost of a small decrease in accuracy caused by voltage drop through the divider 150.

The scaled and buffered output voltage measurement 160 is input to a comparator circuit 165. The comparator 165 outputs either a "high" or a "low" output at 170 depending on whether or not the voltage measurement 160 is higher or lower than the reference voltage 140. The reference voltage 140 is set such that it corresponds to the measurement of the maximum allowed output voltage. Thus, the output 170 of comparator 165 is indicative of whether the output voltage at 135 exceeds a safe level. The reference voltage 140 is calculated as $V=Vlimit/Div$ where Div is the factor by which divider 150 divides and Vlimit is the maximum allowed voltage at path 135.

The output current from path 135 passes through sense resistor 190. Sense resistor 190 is typically a small resistance value, below 20 Ohms, in order to minimize the amount of voltage drop it creates in the current path. Differential amplifier 215 is a shunt current amplifier which multiplies the difference between its two inputs by a fixed gain factor. Current flowing through resistor 190 will cause a potential difference to develop between its two terminals, according to Ohm's law $V=IR$. Thus, the voltage V across 190 will be directly proportional to the output current I. The voltage across resistor 190 will typically be small, and thus amplification by 215 is used to scale it into a usable signal with better signal to noise characteristics. Thus, signal 205 consists of a voltage that corresponds linearly to the amount of current being applied to the patient, according to the equation $V=I*R*A$, where V is the voltage at 205, I is the output current and A is the voltage gain of the amplifier 215.

The current measurement process detailed in the preceding paragraph is duplicated for the current returning to the device from the patient 240. As before, the current causes a voltage difference across resistor 280, and this voltage is amplified by differential amplifier 285 and output as a voltage corresponding to the measured current at 290. This second measurement of current along the same current loop provides redundancy, the ability to detect abnormal sensor performance, and ability to make additional useful determinations about the treatment being applied.

Current measurements 205 and 290, representing before and after transmission through the patient 240, are used to perform two safety checks. Firstly, the current measurements are checked individually at the output of comparators 185 and 300 to ensure they do not exceed a pre-determined maximum current value. Secondly, the two measurements are compared to each other to ensure that they do not differ significantly, as in a system operating normally these measurements will be approximately the same, as they are measured along the same current loop. In an ideal or "perfect" system, these measurements would be identical. The test for maximum current value is carried out using comparator 185 for the outgoing current and comparator 300 for the returning current. Comparators 185 and 300 take as inputs reference signals 180 and 295 respectively. Reference signals 180 and 295 are set such that their voltage corresponds to the voltage that would be measured for the pre-determined maximum allowed current. Thus, reference voltages are set according to the equation $Vref=Ilimit*R*A$ where Vref is the output of 180 or 295, Ilimit is the pre-determined maximum allowed current, R is the value of the respective sense resistor 190,280, and A is the voltage gain of the respective differential amplifier 215,285. As such, comparator 185 will output a signal 195 corresponding to whether or not the outgoing current has exceeded the maximum value, and comparator 300 will output a signal 270 corresponding to whether the returning current has exceeded the maximum value.

In order to test for a discrepancy between the outgoing and returning current measurements, 205 and 290 respectively, the difference between the two measurements is amplified by the differential amplifier 245. The amplified discrepancy value 250 is compared at comparator 255 to a reference voltage discrepancy 220 representing the maximum allowable difference between the two measurements. The reference 220 is set using knowledge of the expected tolerance and variations in the signals involved, including the tolerance of resistors 190 and 280, offset tolerances of amplifiers 215, 285 and 245, and other expected inaccuracies. Reference 220 is set such that it represents a discrepancy higher than could be produced by chance in a functional system with components at their worst-case tolerances. As such, the signal 235 represents whether or not measurements 205 and 290 are different to a magnitude that represents an abnormal condition.

The controller 120 may also output a signal 125 that indicates it has determined an abnormal or unsafe condition to have occurred. Conditions flagged by the controller 120 may include failure of the controller 120 itself such as might be indicated by an internal watchdog timer module, an indication from the operator that something has gone wrong, a detected failure of any of the device power supplies or detection that the electrode interface to the patient is poor or disconnected.

In one embodiment, the controller 120 and each of the comparators 165, 185, 255 and 300 output a "high" signal or "1" when the signals have exceeded the respective maximum reference value.

Signals 125, 170, 195, 235 and 270 thus all represent the occurrence of various error conditions. The signals are logically combined at gate 210 to produce a single signal 305 that is indicative of any of the previously discussed error conditions. The polarity of signal 305 is set by gate 210 such that it is "low" or 0 volts in an error state, and "high" in a normal state. Thus, failure of the power supply of the error detecting logic, or failure of gate 210 to output a value will by default represent an error condition on output 305 to any following circuits. Similarly, pull-down resistor 175 is used to ensure that a damaged or powered down set of gate 210 with output 305 left floating will be pulled to 0 volts, representing an error condition.

Error signal output 305 is passed into a latch circuit, in order to ensure that any temporary or intermittently occurring errors will hold the system into a safe disabled state. The latch circuit consisting of 315, 320, 335, 345 and their wiring is one possible embodiment, constituting a well-known inverted set/reset (Inverted SR) latch configuration. In one embodiment, the latching of the error detector 38 cannot be reset while an error condition is ongoing. Many other known latch configurations are viable and could be substituted. Low pass filters 315 and 335 at the latch inputs are used to ensure that overly brief glitches caused by conducted noise or other transients not representing a safety hazard do not cause the device to be locked into an error state.

Logic 330 and 340 is used in order to ensure that the controller 120 may not reset the error latch, via signal 355, if there is already an error condition currently occurring, as determined on signal 305. The error latch is reset by a "low" or "0" signal through filter 335. Inverter 330 outputs a version of error signal 305 in which a "high" signal or "1" represents an error condition. By combining the reset signal 355 with the output of inverter 330, OR logic 340 outputs the "low" reset signal to the error latch only when both reset signal 355 is "low" and the output of 330 is "low". If the output of inverter 330 is "high", an error is present, and the output of OR logic 340 must also be "high" regardless of reset signal 355. Through this logic, the error latch is prevented from being reset while an error is occurring. In embodiments using other error latch configurations, different combinations of logic gates will be necessary at the latch reset input in order to prevent reset from occurring during an error.

In one embodiment filters 315 and 335 may be configured to have time constants long enough to filter out detected errors which are so brief that they do not constitute a problem. For example, if the connection to the patient 240 is disconnected, the output 135 will move to its maximum voltage, due to the open circuit it is presented with. If the circuit is then quickly closed again, there will be a finite amount of time taken for the voltage at 135 to reduce to the amount needed to produce the programmed amount of current—i.e. the current source 115 cannot respond to changes in impedance infinitely fast. Thus, there could be instances in a fully functional device where the output current slightly exceeds the maximum current for trivially brief periods of time—on the order of nanoseconds. If the response of the error detecting circuitry is sufficiently fast, these brief transients may be detected as errors, even though they do not truly represent an unsafe state of the device. As such, filters 315 and 335 may be configured so as to remove these transients without compromising patient safety and without interrupting device operation. Depending on system conditions, in other embodiments time periods may be adjusted to microseconds, for example, to avoid brief current spikes.

Output 350 from the latch is a logical "high" when there are no errors present. Pull-down resistor 325 is used to ensure that a damaged or powered down latch circuit that leaves its output floating will not allow the device to be enabled. Output 350 is used to enable output to the patient at interruptors 230 and 265. Interruptors 230 and 265 may be embodied as solid state relays or other electrically controllable switches, as described above. When both interruptors 230 and 265 are in an open state, the patient 240 is isolated from the rest of the device electronics by a substantial amount of impedance with a very high breakdown voltage.

The latched error output signal 350 may also be used to disable the power supply that powers the output current, as illustrated by signal 105 being used to disable power supply 110. Output 350 may further be connected to the controller 120, as at 100, to inform any controlling software of the error, so that it may take any further desired actions—such as informing the device operator.

In one embodiment, further redundant protection may be provided to the patient using passive circuit elements, such as low-current fuses 225 and 260, and transient voltage suppression (TVS) components, such as the suppression diodes 200 and 275. Typical fuses available on the market are not adequate to provide protection in a tDCS device on their own, as the maximum currents used are typically below the tripping value of even the smallest commercially available fuses. As such, active protection elements as have been illustrated provide faster, more accurate protection against fault conditions, however fusing elements still provide desirable redundancy against significant fault conditions.

An error counter 130 connected to the controller 120 may also be implemented in order to monitor frequency of errors and ensure that errors are not continually occurring and being reset.

DESCRIPTION OF METHOD

In order to safely operate the tDCS device, the following steps are undertaken. The tDCS device is turned on and a set of electrodes connected to the device are applied to a patient. Once the electrodes are correctly applied, the current source of the device may be switched on. The output current of the device is monitored to check for abnormal measurements. Abnormal output current measurements may consist of a measurement that is too high, a measurement that is too low or a measurement that is oscillating or changing in an unintended fashion. If the output current is determined to be abnormal, the current to the patient is interrupted. Similarly, the current returning from the patient may be monitored, and the current to the patient interrupted if this measurement is abnormal in any of the listed fashions. As the output and returning current measurements should be approximately equal, accounting for various non-ideal and properties of the measurement, the current to the patient may be interrupted if the difference in magnitude between the output and returning current is too great or if the comparison of the two is abnormal in any other way. A microcontroller may also directly signal for the current to the patient to be interrupted if, for example, it experiences an abnormal operating state or becomes stuck in a program loop. A latching circuit may be used to hold the device in an interrupted state until the device or latch circuit is reset. The output or returning voltage may also be monitored, and the current to the patient interrupted if the voltage is abnormal. An abnormal voltage may be too high, too low, or be oscillating or changing in an unintended fashion. The current to the patient may also be interrupted if the output voltage divided by the output or returning current is too high or otherwise abnormal, as this calculation represents the resistance of the electrical path through the patient.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A device for transcranial stimulation, comprising:
   a. an adjustable current source configured to provide a stimulation current;
   b. a first electrode connected to the current source for electrical connection to a patient;
   c. a second electrode connected to the current source for electrical connection to the patient;
   d. a first current interrupter configured to open a switch and interrupt current flow between the current source and the first electrode, the first current interrupter connected between the adjustable current source and the first electrode and separate and independent of the current source;
   e. an output monitor connected between the current source and the first electrode configured to monitor current to the patient;
   f. a second current interrupter separate and independent of the current source configured to open a switch and interrupt current flow between the current source and the second electrode connected between the adjustable current source and the second electrode;
   g. a return monitor connected between the current source and the second interrupter configured to monitor return current from the patient;
   h. an error detector, wherein the output monitor and return monitor are in communication with the error detector, and the error detector provides a signal to at least one of the first and second interrupters to interrupt current to the patient when an abnormal current is detected by at least one of the output monitor and return monitor, wherein the error detector is a latching error detector configured to hold the device in an interrupted state if an error occurs during operation, even if the device is turned off and on again, wherein when the output monitor detects an abnormal current it signals the first interrupter, which interrupts current to the patient.

2. The device of claim 1, wherein the error detector comprises a comparator configured to compare magnitudes of differences of signals of the output monitor and return monitor.

3. The device of claim 1, wherein the error detector indicates normal operation with a high signal and abnormal operation with a low signal, such that if the error detector receives no power an abnormal operation is signaled.

4. The device of claim 1, further comprising an error counter in communication with a controller configured to monitor a frequency of errors.

5. A device for transcranial stimulation, comprising:
   a. an adjustable current source configured to provide a stimulation current;
   b. a first electrode connected to the current source for electrical connection to a patient;
   c. a second electrode connected to the current source for electrical connection to the patient;
   d. a first current interrupter configured to open a switch and interrupt current flow between the current source and the first electrode, the first current interrupter connected between the adjustable current source and the first electrode and separate and independent of the current source;
   e. an output monitor connected between the current source and the first electrode configured to monitor current to the patient;
   f. a second current interrupter separate and independent of the current source configured to open a switch and interrupt current flow between the current source and the second electrode connected between the adjustable current source and the second electrode;
   g. a return monitor connected between the current source and the second interrupter configured to monitor return current from the patient;
   h. an error detector, wherein the output monitor and return monitor are in communication with the error detector, and the error detector provides a signal to at least one of the first and second interrupters to interrupt current to the patient when an abnormal current is detected by at least one of the output monitor and return monitor, wherein the error detector is a latching error detector configured to hold the device in an interrupted state if an error occurs during operation, even if the device is turned off and on again, wherein when the output monitor detects an abnormal current it signals the first interrupter, which interrupts current to the patient, and wherein the latching error detector cannot be reset while an error condition is ongoing.

\* \* \* \* \*